United States Patent
Jarvis et al.

(10) Patent No.: US 10,204,770 B2
(45) Date of Patent: Feb. 12, 2019

(54) METHOD TO IMPROVE MS/MS SPECTRAL QUALITY FROM MRM TRIGGERED IDA

(71) Applicant: DH Technologies Development Pte. Ltd., Singapore (SG)

(72) Inventors: Michael Jarvis, Alliston (CA); Yves Le Blanc, Newmarket (CA); David M. Cox, Toronto (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 15/754,770

(22) PCT Filed: Aug. 9, 2016

(86) PCT No.: PCT/IB2016/054778
§ 371 (c)(1),
(2) Date: Feb. 23, 2018

(87) PCT Pub. No.: WO2017/037555
PCT Pub. Date: Mar. 9, 2017

(65) Prior Publication Data
US 2018/0269048 A1  Sep. 20, 2018

Related U.S. Application Data

(60) Provisional application No. 62/212,289, filed on Aug. 31, 2015.

(51) Int. Cl.
*H01J 49/00* (2006.01)
*G01N 27/62* (2006.01)

(52) U.S. Cl.
CPC ........ *H01J 49/0036* (2013.01); *G01N 27/624* (2013.01); *H01J 49/004* (2013.01); *H01J 49/0027* (2013.01)

(58) Field of Classification Search
CPC ............... H01J 49/0027; H01J 49/0031; H01J 49/0036; H01J 49/004; G01N 27/622; G01N 27/624
See application file for complete search history.

(56) References Cited

U.S. PATENT DOCUMENTS

2010/0282961 A1* 11/2010 Miller ................... H01J 49/004
250/282
2014/0326870 A1  11/2014 Makarov
(Continued)

FOREIGN PATENT DOCUMENTS

WO  2014076529 A1  5/2014

OTHER PUBLICATIONS

International Search Report and Written Opinion for PCT/IB2016/054778 dated Dec. 1, 2016.

*Primary Examiner* — David E Smith
(74) *Attorney, Agent, or Firm* — John R. Kasha; Kelly L. Kasha; Kasha Law LLC (57) ABSTRACT

Systems and methods are provided for enabling or disabling a DMS device during an IDA method. Each cycle of the method includes a survey scan step, producing a precursor ion mass spectrum, and an MS/MS scan step. During the MS/MS scan step, one or more user-defined MS/MS scans are performed that correspond to compounds of interest found in the precursor ion mass spectrum. With each user-defined MS/MS scan, a DMS enable parameter that determines if the DMS device is enabled or disabled and one or more DMS parameters necessary to enable the DMS device for the corresponding compound of interest are received. During the MS/MS scan step, for each user-defined MS/MS scan, the DMS device is enabled or disabled according to the DMS enable parameter and one or more parameters of the DMS device are set according to the one or more DMS parameters.

15 Claims, 7 Drawing Sheets

(56) References Cited

U.S. PATENT DOCUMENTS

2015/0144778 A1    5/2015  Bonner et al.
2015/0233866 A1    8/2015  Verenchikov
2017/0125235 A1*   5/2017  Green ................ H01J 49/0036

* cited by examiner

FIG. 2 (PRIOR ART)

| COMPOUND OF INTEREST | SCAN TYPE | PRECURSOR MASS | CHARGE | PRODUCT MASS | CHARGE | ... | COLLISION ENERGY |
|---|---|---|---|---|---|---|---|
| INDOMETHOCIN | MRM | 358 | +1 | 139 | +1 | ... | 35 |
| INDOMETHOCIN | EPI | 358 | +1 | N/A | N/A | ... | 35 |
| ... | ... | ... | ... | ... | ... | ... | ... |

300 ⟵

(PRIOR ART)

FIG. 3

| COMPOUND OF INTEREST | SCAN TYPE | PRECURSOR MASS | CHARGE | PRODUCT MASS | CHARGE | ... | COLLISION ENERGY | DMS ENABLE | DMS COV |
|---|---|---|---|---|---|---|---|---|---|
| INDOMETHOCIN | MRM | 358 | +1 | 139 | +1 | ... | 35 | NO | 6 |
| INDOMETHOCIN | EPI | 358 | +1 | N/A | N/A | ... | 35 | YES | 6 |
| ... | ... | ... | ... | ... | ... | ... | ... | ... | ... |

METHOD TO IMPROVE MS/MS SPECTRAL QUALITY FROM MRM TRIGGERED IDA

CROSS REFERENCE TO RELATED APPLICATION

This application claims the benefit of U.S. Provisional Patent Application Ser. No. 62/212,289, filed Aug. 31, 2015, the content of which is incorporated by reference herein in its entirety.

INTRODUCTION

Both qualitative and quantitative information can be obtained from a tandem mass spectrometer. In such an instrument a precursor ion is selected in a mass filter, fragmented, and the product ions are analyzed in a mass analyzer. The entire process of selecting a precursor ion, fragmenting it, and analyzing the resulting product ions by mass-to-charge ration (m/z) is referred to mass spectrometry/mass spectrometry (MS/MS) or an MS/MS scan. The product ion spectrum produced from MS/MS can be used to identify a compound (the precursor ion) in a sample, and the intensity of one or more product ions can be used to quantitate the amount of the compound present in the sample.

Information dependent analysis (IDA) is a flexible tandem mass spectrometry method in which a user can specify criteria for performing MS/MS while a sample is being introduced into the tandem mass spectrometer. For example, in an IDA method a precursor ion or mass spectrometry (MS) survey scan is performed to generate a precursor ion peak list. The user can select criteria to filter the peak list for a subset of the precursor ions on the peak list. MS/MS is then performed on each precursor ion of the subset of precursor ions. A product ion spectrum is produced for each precursor. MS/MS is repeatedly performed on the precursor ions of the subset of precursor ions the sample is being introduced into the tandem mass spectrometer. The sample is introduced through an injection or chromatographic run, for example.

Generally, two types of MS/MS are performed during an IDA method. In the first type, a single precursor ion is selected and fragmented, and an entire mass range of product ions is mass analyzed. This type of MS/MS scan is referred to as full scan MS/MS or a full product ion MS/MS scan. Full scan MS/MS is typically used for qualitative analysis. In other words, full scan MS/MS is typically used to identify a precursor ion from a pattern of product ions.

In the second type of MS/MS, a single precursor ion is selected and fragmented, a single product ion is then selected from the resulting product ions, and only the selected production ion is mass analyzed. This type of MS/MS is referred to as multiple reaction monitoring (MRM) or selected reaction monitoring (SRM) or as an MRM or SRM scan or transition. MRM is typically used for quantitative analysis. In other words, MRM is typically used to quantify the amount of a precursor ion in a sample from the intensity of a single product ion.

Some tandem mass spectrometers, such as SCIEX's QTRAP®, allow IDA methods to perform MRM and full scan MS/MS in a single experiment. As a result, both quantitative and qualitative data can be acquired in a single experiment. This is very useful for multi-analyte screening methods, which include drug testing and pesticide screening methods, among others.

Unfortunately, full scan MS/MS spectra that are acquired in an IDA method are susceptible to isobaric interferences. Isobaric interference occurs when a sample contains another compound that has a similar m/z as the analyte, or compound of interest. The interference causes a spectrum of the compound of interest to include product ions of the interfering compound. These additional product ions, in turn, can produce poor results when the spectrum is searched against an existing database of full scan MS/MS spectra for known compounds.

For IDA methods, differential mobility spectrometry (DMS) has been shown to be able to resolve isobaric interferences that cannot be separated by full scan MS/MS. Specifically, AB SCIEX's SelexION™ ion mobility technology has been utilized to enhance the quality of m/z analysis by pre-separating ions of similar m/z, thereby removing these isobaric interferences and improving the mass spectral library searching scores.

However, the mass spectrometry industry, to date, has been unable to apply DMS to an IDA method where a large number of different compounds are present in a sample. This is because DMS causes the cycle time to be unacceptably large, due to the requirement of an additional pause time after each MRM, and after each full scan MS/MS. Therefore, the mass spectrometry industry has found it impractical to use DMS in IDA methods where MRM and full scan MS/MS are performed and where a sample may contain a large number of different compounds, because of the time constraints imposed by DMS.

SUMMARY

A system is disclosed for enabling or disabling a differential mobility spectrometry (DMS) device during an information dependent acquisition (IDA) experiment based on each mass spectrometry/mass spectrometry (MS/MS) scan performed. The system includes an ion source, a DMS device, a mass spectrometer, and a processor.

The ion source ionizes a sample producing an ion beam. The DMS device receives the ion beam from the ion source. The mass spectrometer receives the ion beam from the DMS device and performs one or more cycles of an IDA experiment on the ion beam. Each cycle of the one or more cycles includes a survey scan step that produces a precursor ion mass spectrum. Each cycle also includes an MS/MS scan step. During the MS/MS scan step, one or more user-defined MS/MS scans of a plurality of user-defined MS/MS scans are performed that correspond to compounds of interest found in the precursor ion mass spectrum.

The processor receives from a user, with each user-defined MS/MS scan of the plurality of user-defined MS/MS scans, a corresponding compound of interest and a plurality of parameters. The plurality of parameters include a DMS enable parameter that determines if the DMS device is enabled or disabled for the user-defined MS/MS scan and one or more DMS parameters necessary to enable the DMS device for the corresponding compound of interest of the user-defined MS/MS scan.

During the MS/MS scan step, for each user-defined MS/MS scan of the one or more user-defined MS/MS scans, the processor enables or disables the DMS device according to the DMS enable parameter of the user-defined MS/MS scan and sets one or more parameters of the DMS device according to the one or more DMS parameters of the user-defined MS/MS scan.

A method is disclosed for enabling or disabling a DMS device during an IDA experiment based on each MS/MS scan performed.

A sample is ionized using an ion source, producing an ion beam. The ion beam is received from the ion source using a DMS device. The ion beam is received from the DMS device and one or more cycles of an IDA experiment are performed on the ion beam using a mass spectrometer. Each cycle of the one or more cycles includes a survey scan step that produces a precursor ion mass spectrum and an MS/MS scan step. During the MS/MS scan step, one or more user-defined MS/MS scans of a plurality of user-defined MS/MS scans are performed that correspond to compounds of interest found in the precursor ion mass spectrum.

With each user-defined MS/MS scan of the plurality of user-defined MS/MS scans, a corresponding compound of interest and a plurality of parameters are received from a user. The plurality of parameters include a DMS enable parameter that determines if the DMS device is enabled or disabled for the user-defined MS/MS scan and one or more DMS parameters necessary to enable the DMS device for the corresponding compound of interest of the user-defined MS/MS scan using a processor.

During the MS/MS scan step, for each user-defined MS/MS scan of one or more user-defined MS/MS scans, the DMS device is enabled or disabled according to the DMS enable parameter of the user-defined MS/MS scan and one or more parameters of the DMS device are set according to the one or more DMS parameters of the user-defined MS/MS scan using the processor.

A computer program product is disclosed that includes a non-transitory and tangible computer-readable storage medium whose contents include a program with instructions being executed on a processor so as to perform a method for enabling or disabling a DMS device during an IDA experiment based on each MS/MS scan performed. In various embodiments, the method includes providing a system, wherein the system comprises one or more distinct software modules, and wherein the distinct software modules comprise a control module.

The control module instructs an ion source to ionize a sample, producing an ion beam. The control module instructs a DMS device to receive the ion beam from the ion source. The control module instructs a mass spectrometer to receive the ion beam from the DMS device and perform one or more cycles of an IDA experiment on the ion beam. Each cycle of the one or more cycles includes a survey scan step that produces a precursor ion mass spectrum and an MS/MS scan step. During the MS/MS scan step, one or more user-defined MS/MS scans of a plurality of user-defined MS/MS scans are performed that correspond to compounds of interest found in the precursor ion mass spectrum.

The control module receives from a user, with each user-defined MS/MS scan of the plurality of user-defined MS/MS scans, a corresponding compound of interest and a plurality of parameters. The plurality of parameters include a DMS enable parameter that determines if the DMS device is enabled or disabled for the user-defined MS/MS scan and one or more DMS parameters necessary to enable the DMS device for the corresponding compound of interest of the user-defined MS/MS scan. During the MS/MS scan step, for each user-defined MS/MS scan of one or more user-defined MS/MS scans, the control module enables or disables the DMS device according to the DMS enable parameter of the user-defined MS/MS scan and sets one or more parameters of the DMS device according to the one or more DMS parameters of the user-defined MS/MS scan.

These and other features of the applicant's teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

Figure 1:
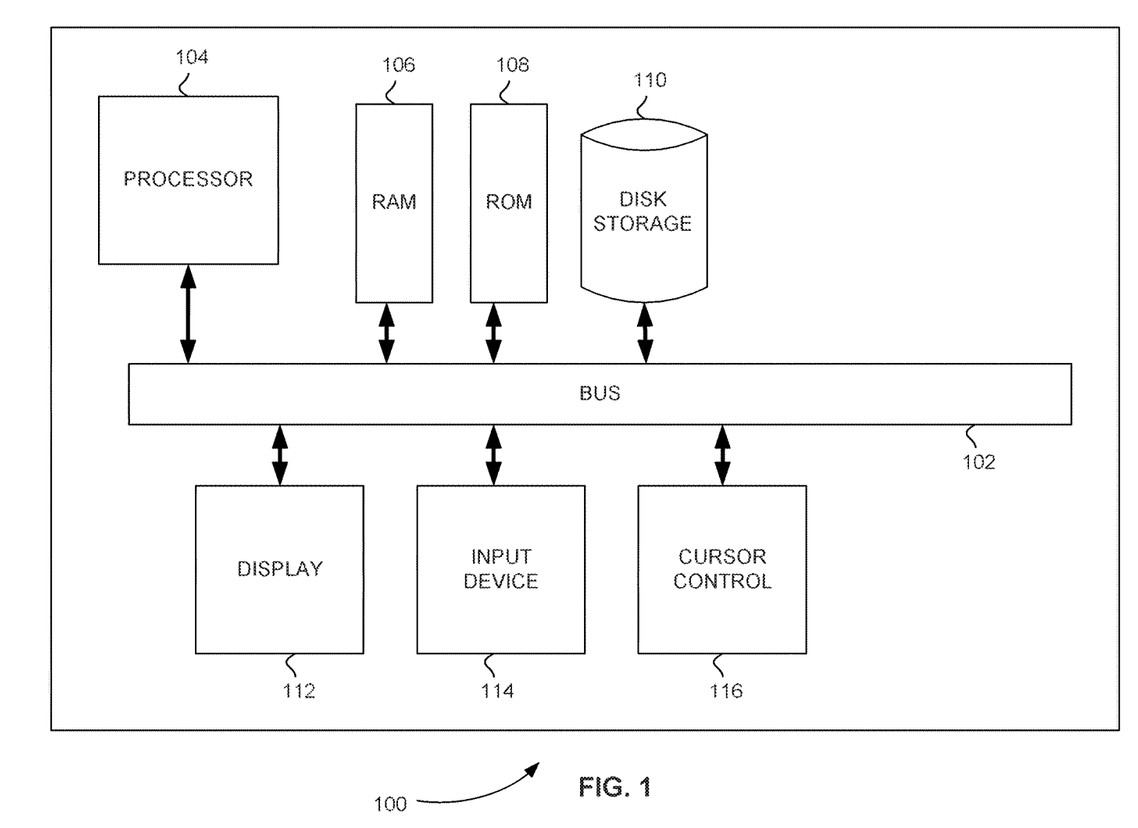
FIG. 1 is a block diagram that illustrates a computer system, upon which embodiments of the present teachings may be implemented.

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

IDA Triggered DMS Mode Switching

As described above, full scan spectrometry/mass spectrometry (MS/MS) spectra that are acquired in an IDA method are susceptible to isobaric interferences, i.e., where the precursor ion of interest is sampled simultaneously to concomitant interference that will generate additional fragment ions. Differential mobility spectrometry (DMS) has been shown to be able to resolve isobaric interferences that cannot be separated by full scan MS/MS in an IDA method. However, the mass spectrometry industry has found that using DMS in IDA methods where MRM and full scan MS/MS are performed and where a sample may contain a large number of different compounds, imparts significant time constraints on an LC time scale because of the DMS.

Figure 2:
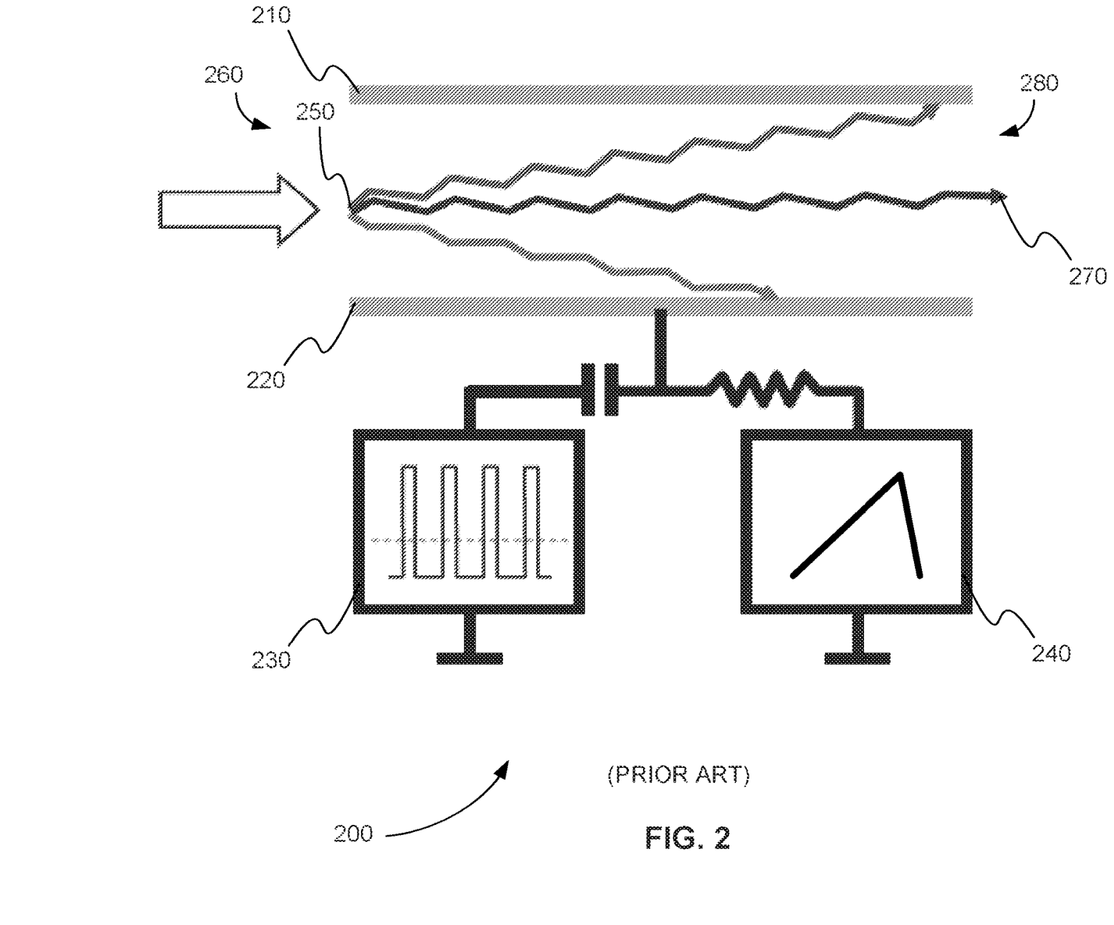
FIG. 2 is a schematic diagram of an exemplary differential mobility spectrometry (DMS) device.

FIG. 2 is a schematic diagram of an exemplary DMS device 200. DMS device 200 includes two parallel flat plates, plate 210 and plate 220. Radio frequency (RF) voltage source 230 applies an RF separation voltage (SV) across plate 210 and plate 220, and direct current (DC) voltage source 240 applies a DC compensation voltage (CoV) across plate 210 and plate 220. Ions 250 enter DMS device 200 in a transport gas at opening 260. The separation of ions 250 in DMS device 200 is based upon differences in their migration rates under high versus low electric fields.

Unlike traditional ion mobility, ions 250 are not separated in time as they traverse the device. Instead, ions 250 are separated in trajectory based on the difference in their mobility between the high field and low field portions of applied RF voltage source 230. The high field is applied between plate 210 and plate 220 for a short period of time, and then a low field is applied in the opposite direction for a longer period of time. Any difference between the low-field and high-field mobility of an ion of a compound of interest causes it to migrate towards one of the plates. The ion is steered back towards the center-line of the device by the application of a second voltage offset, known as the CoV of DC voltage source 240, a compound-specific parameter that can be used to selectively filter out all isobaric interferences and many others. Rapid switching of the CoV allows the user to concurrently monitor many different compounds. Ions 270 selected by the combination of SV and CoV, leave DMS device 200 through opening 280 to the remainder of the mass spectrometer (not shown). DMS device 200 is located between an ion source (not shown) and the remainder of the mass spectrometer, for example.

In general, DMS device 200 has two modes of operation. In the first mode, DMS device 200 is on, SV and CoV voltages are applied, and ions are separated. This is, for example, the enabled mode.

In the second mode of operation, DMS device 200 is off, the SV is set to zero and ions 250 are simply transported from entrance opening 260 to exit opening 280. This is, for example, the disabled or transparent mode of DMS device 200.

In the enabled mode, DMS device 200 can acquire data for a single MRM transition in 25 milliseconds (ms), for example, including an inter-scan pause time of 20 ms. In transparent mode, the delay through DMS device 200 is negligible.

Currently, the mass spectrometry industry only allows an IDA method to use a DMS device in the enabled mode or in the transparent mode for an entire experiment. If the IDA method only performs one or more MRM scans, the DMS device is placed in the transparent mode. MRM scans are generally free of isobaric interferences, due to the enhanced selectivity of MRM. In other words, because the product ion of the compound of interest is also selected in MRM, the product ions of other compounds with similar precursor m/z have no effect.

If IDA method performs only a few MRM scans and a few full product ion MS/MS scans, the DMS device can be placed in the enabled mode. As described above, the enabled DMS device can remove effects of isobaric precursor ion interferences from the full scan MS/MS spectra. Because the DMS device is enabled, it also affects the MRM scans. It does not generally improve results of the MRM scans, at least not on the main MRM which is typically tuned for selectivity (this may not be the case for secondary and tertiary confirmatory MRM used in some application). It does, however, increase the times between scans. As described above, the inter-scan pause time required by a DMS device is on the order of 20 ms. Without a DMS device, an IDA method can perform multiple MRMs with a pause time between MRMs of between 3 and 5 ms. The added delay caused by the enabled DMS device, therefore, considerably increases the time between MRM scans.

In an IDA experiment, a number of MRM scans from a list of MRM scans are performed sequentially. A single pass through the entire MRM list is referred to the survey cycle. The overall cycle (sum of survey cycle and dependent cycle) can also include one or more full product ion MS/MS scans that are triggered after the product ion intensity of an MRM scan is found above a threshold value. The IDA experiment typically performs multiple cycles as a sample is being introduced into the tandem mass spectrometer. The overall cycle time is typically adjusted to yield an optimum number of data point across the LC peak to provide more accurate quantitative measurements.

When an IDA experiment includes only a small number of compounds of interest, the number of MRM scans is also small. Therefore, the time it takes to perform an overall cycle is small. However, as the number of compounds of interest increases, so does the number of MRM scans, in turn, increasing the overall cycle time. Because the enabled DMS device significantly increases the delay between MRM scans, it also increases the overall cycle time. For small number of MRM scans, the effect on the overall cycle time is small. However, when the number of MRM scans increases to a certain point, the overall cycle time may get so large that compounds of interest are missed from a separating sample, for example.

As a result, as described above, the mass spectrometry industry has found limiting to use DMS in IDA methods where MRM and full scan MS/MS are performed and where a sample may contain a large number of different compounds, because of the time constraints imposed by activating the DMS for all MRM.

In various embodiments, an IDA method enables or disables a DMS device according to the parameters of the MS/MS scan being performed. In a typical IDA experiment, a user selects the parameters of each MS/MS scan to be run for each compound of interests. A user can select these parameters either directly or indirectly. A user can select these parameters directly by uploading a file that specifies each MS/MS scan and its parameters, for example. A user can select these parameters indirectly by selecting options in a user interface that sets the actual parameter values, for example.

Figure 3:
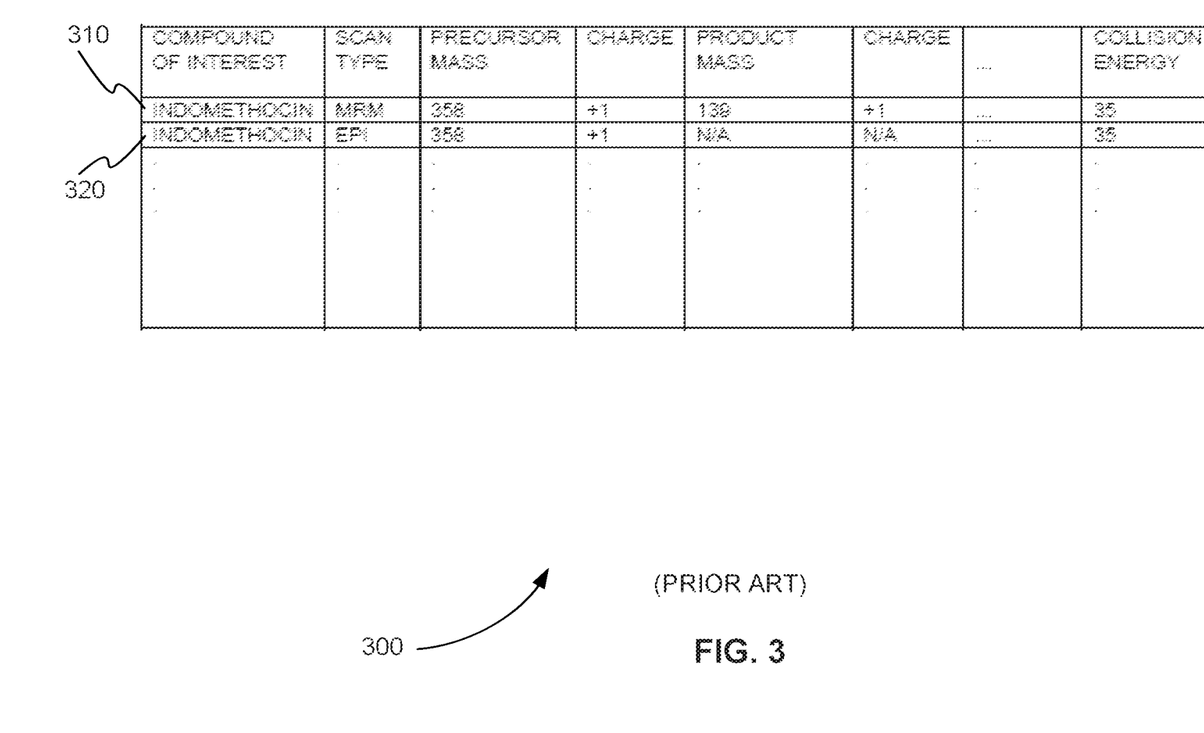
FIG. 3 is an exemplary list of mass spectrometry/mass spectrometry (MS/MS) scan parameters for an information dependent analysis (IDA) experiment.

FIG. 3 is an exemplary list 300 of MS/MS scan parameters for an IDA experiment. The user-defined MS/MS scans are shown in the rows of list 300, and the parameters for scan are shown in the columns of list 300. List 300 includes only the CE as parameters for a row. However, the parameters can include other parameters that are compound specific (e.g. declustering potential (DP)). List 300 includes only two user-defined MS/MS scans, 310 and 320. However, the list can include hundreds of user-defined MS/MS scans, for example.

Each user-defined MS/MS scan has a corresponding compound of interest. The corresponding compound of interest for scans 310 and 320 is indomethacin, for example. In an IDA experiment, each cycle includes at least one mass spectrometry (MS) survey scan followed by multiple MS/MS scans. The multiple MS/MS scans are selected from a list, such as list 300, of user-defined MS/MS scans based on the results of the MS survey scan. Therefore, each MS/MS scan is a secondary scan of the MS survey scan. The multiple MS/MS scans are selected based on the compounds of interest found in the precursor ion spectrum produced by the MS survey scan.

For example, if an MS survey scan detects indomethacin in a sample that is above a predetermined threshold level, the IDA method will select user-defined MS/MS scans 310 and 320 for execution during that cycle. MS/MS scan 310 is an MRM scan. In addition to the precursor ion parameters, MS/MS scan 310 includes product ion parameters. MRM scans are generally performed in each cycle of the IDA method until the precursor ion is no longer present in the MS survey scan or until the MRM scan produces a product ion intensity for the precursor ion and the product ion pair (MRM pair) that is above a predetermined threshold level.

Some IDA methods allow MRM triggered MS/MS scans. For example, the user-defined MS/MS scans of a list, such as list 300, may additionally include parameters that identify each user-defined MS/MS scan as a primary or secondary scan. The parameters also link secondary scans to primary scans. For example, user-defined MS/MS scan 310 can be designated as a primary MRM scan using a parameter (not shown) of list 300. The parameter also designates, for example, user-defined MS/MS scan 320 as the secondary scan. As a result, whenever user-defined MS/MS scan 310 is executed and produces results that have product ion intensities above a predetermined threshold level, user-defined MS/MS scan 320 is triggered or performed.

User-defined MS/MS scan 320 is a full product ion MS/MS scan, which can also be called an enhanced product ion (EPI) scan. Full product ion MS/MS scans produced an entire product ion spectrum for a precursor ion of the compound of interest. As a result, full product ion MS/MS scans are used, for example, for comparison with a database of known compounds that includes a known product ion spectrum for each known compound. By comparing the measured product ion spectrum to the known product ion spectrum, the measured compound can be identified. As described above, however, full product ion MS/MS scans, such as user-defined MS/MS scan 320, can include interfering production ions generated from precursor isobaric interferences.

As shown in list 300, user-defined MS/MS scans 310 and 320 also include device parameters, such as collision energy. In various embodiments, parameters are added to each user-defined MS/MS scan that allow a DMS device to be switched on and off during an IDA experiment based on the MS/MS scan being performed.

Figure 4:
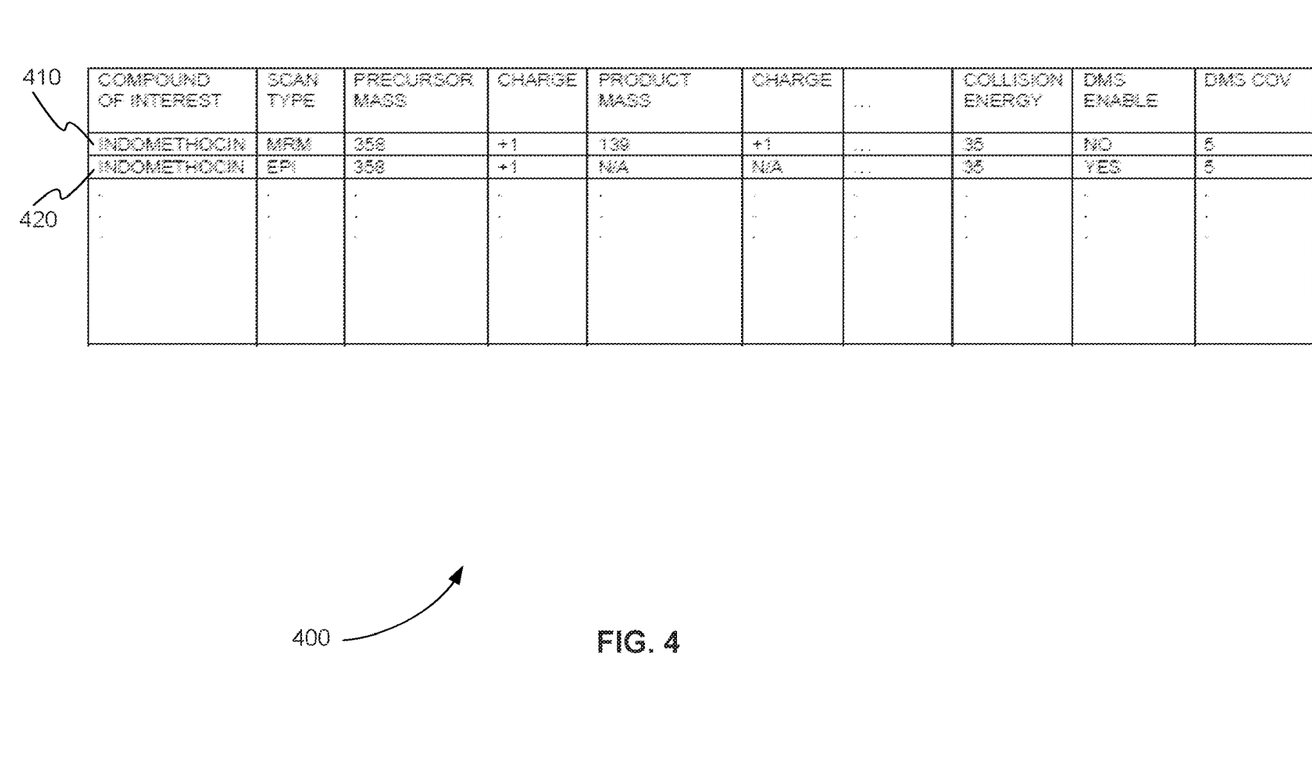
FIG. 4 is an exemplary list of MS/MS scan parameters for an IDA experiment that includes parameters that allow a DMS device to be enabled or disabled during the IDA experiment based on the MS/MS scan being performed, in accordance with various embodiments.

FIG. 4 is an exemplary list 400 of MS/MS scan parameters for an IDA experiment that includes parameters that allow a DMS device to be enabled or disabled during the IDA experiment based on the MS/MS scan being performed, in accordance with various embodiments. List 400 includes two user-defined MS/MS scans, 410 and 420, similar to the two user-defined MS/MS scans of FIG. 3. In addition, user-defined MS/MS scans 410 and 420 include an enable DMS parameter and a DMS compensation voltage (CoV) parameter. The enable DMS parameter allows a user to specify if a DMS device should be switched on or switched off for the user-defined MS/MS scan. The DMS CoV parameter provides the CoV value that should be used by the DMS, when it is enabled, to select the compound of interest of the user-defined MS/MS scan. List 400 can also be expanded to include other DMS parameters such as, but not limited to SV (separation voltage).

In various embodiments, the enable DMS parameter can be a binary parameter that simply indicates whether or not the DMS device is to be enabled. A binary yes or no flag is shown in list 400, for example. In list 400, user-defined MS/MS scan 410 includes an enable DMS parameter with a yes value that enables, or turns on, the DMS device. In list 400, user-defined MS/MS scan 420 includes an enable DMS parameter with a no value that disables, or turns off, the DMS device.

In various embodiments, the enable DMS parameter can be the SV voltage. As described above, if the RF SV and DC CoV voltages are set to zero, a DMS device simply allows all ions to pass through. As a result, if the RF SV and DC CoV voltages are set to zero, the DMS device is placed in transparent mode and is effectively disabled or switched off. If the RF SV voltage is set to an RF voltage needed to select the corresponding compound of interest, along with the DC CoV voltage of the user-defined MS/MS scan, the DMS device is effectively enabled or switched on.

In various embodiments, the SV voltage is defined in a DMS SV parameter and not the enable DMS parameter. In this case, list 400 includes an additional column for the DMS SV parameter (not shown), for example.

In various embodiments, the enable DMS parameter can be set and reset dynamically during an IDA method. For example, a user-defined full product ion MS/MS scan can include an enable DMS parameter that has a value that disables the DMS device. During an IDA method, the user-defined full product ion MS/MS scan can be performed producing a measured product ion spectrum. The measured product ion spectrum can then be compared to a known product ion spectrum for the compound of interest corresponding to the user-defined full product ion MS/MS scan (real time MSMS spectral comparison to library spectrum). The known product ion spectrum is found by querying a database of known compounds and their product ion spectra using the compound of interest corresponding to the user-defined full product ion MS/MS scan. If the known product ion spectrum does not match the measured product ion within a predetermined threshold level, the DMS enable parameter of the user-defined full product ion MS/MS scan is set to a value that enables the DMS device for subsequent scans of the user-defined full product ion MS/MS scan.

In various embodiments, the enable DMS parameter can be set and reset dynamically during an IDA method. For example, a user-defined secondary set of MRM includes an enable DMS parameter that has a value that disables the DMS device. During an IDA method, the user-defined MRMs can be performed producing a measured series of MRM ratio. The measured MRM ratio can then be compared to a known MRM ratio for the compound of interest corresponding to the user-defined expected MRM ratio (real time MRM ratio comparison to library values). The known MRM ratio is found by querying a database of known compounds and their MRM ration using the compound of interest corresponding to the user-defined full MRM ratio. If the known MRM ratio does not match the measured MRM ratio within a predetermined threshold level, the DMS enable parameter of the user-defined MRM ratio is set to a value that enables the DMS device for subsequent scans of the user-defined MRM scan.

System for IDA Triggered DMS Switching

Figure 5:
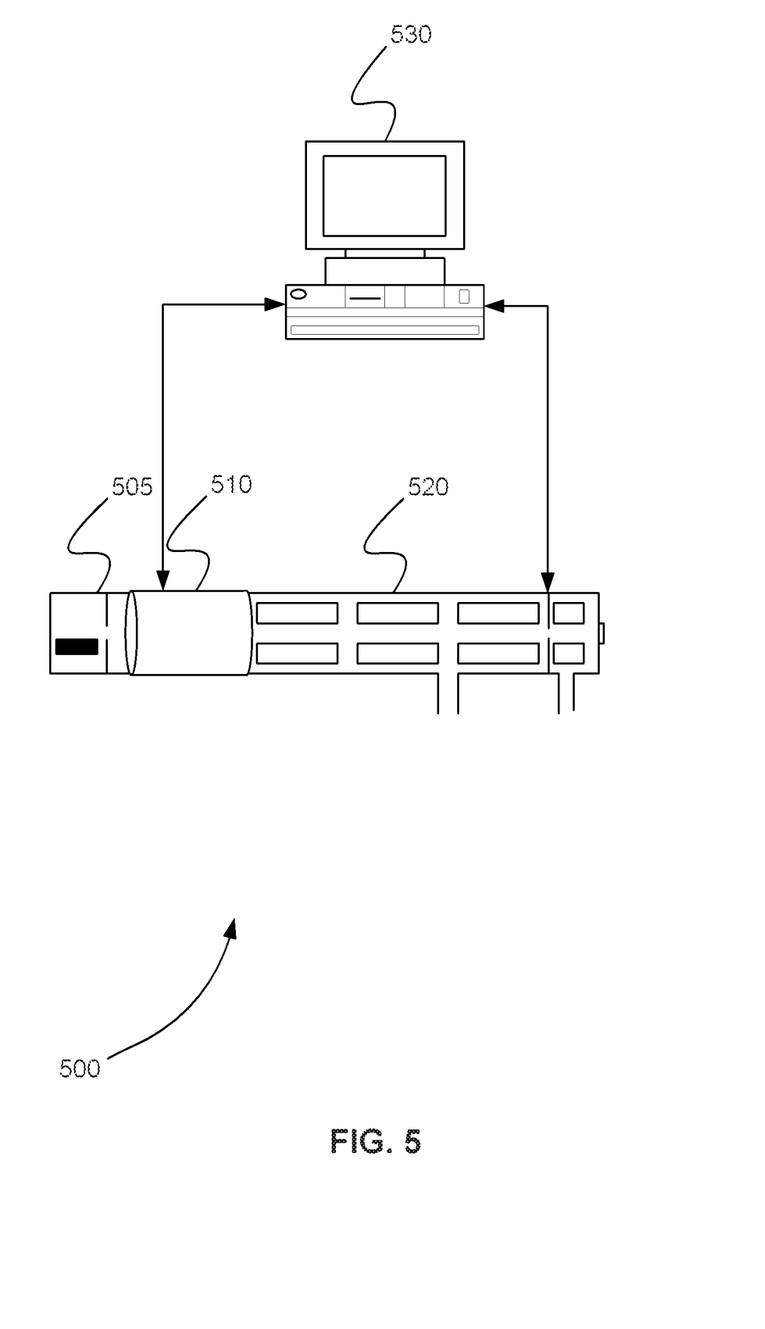
FIG. 5 is a schematic diagram showing a system for enabling or disabling a DMS device during an IDA experiment based on each MS/MS scan performed, in accordance with various embodiments.

FIG. 5 is a schematic diagram showing a system 500 for enabling or disabling a DMS device during an IDA experiment based on each MS/MS scan performed, in accordance with various embodiments. System 500 includes ion source 505, DMS device 510, mass spectrometer 520, and processor 530.

Ion source 505 ionizes a sample producing an ion beam. System 500 can also include a sample introduction device (not shown) that presents the sample to the ion source. The sample introduction device can provide a sample to ion source 505 using one of a variety of techniques. These techniques include, but are not limited to, gas chromatography (GC), liquid chromatography (LC), capillary electrophoresis (CE), or flow injection analysis (FIA).

DMS device 510 receives the ion beam from ion source 505. DMS device 510 can be a SelexION™ device, for example.

Mass spectrometer 520 is a tandem mass spectrometer and can include one or more physical mass filters and one or more physical mass analyzers. A mass analyzer of mass spectrometer 520 can include, but is not limited to, a time-of-flight (TOF), quadrupole, an ion trap, a linear ion trap, an orbitrap, or a Fourier transform mass analyzer.

Mass spectrometer 520 receives the ion beam from DMS device 510 and performs one or more cycles of an IDA experiment on the ion beam. Each cycle of the one or more cycles includes a survey scan step that produces a precursor ion mass spectrum. Each cycle also includes an MS/MS scan step. During the MS/MS scan step, one or more user-defined MS/MS scans of a plurality of user-defined MS/MS scans are performed that correspond to compounds of interest found in the precursor ion mass spectrum. The plurality of user-defined MS/MS scans can include one or more user-defined MRM scans and/or one or more user-defined full product ion MS/MS scans.

Processor 530 can be, but is not limited to, the system of FIG. 1, a computer, microprocessor, or any device capable of sending and receiving control information and data to and from DMS device 510 and mass spectrometer 520 and processing data. Processor 530 is in communication with DMS device 510 and mass spectrometer 520.

Processor 530 receives from a user, with each user-defined MS/MS scan of the plurality of user-defined MS/MS scans, a corresponding compound of interest and a plurality of parameters. The plurality of parameters include a DMS enable parameter that determines if the DMS device is enabled or disabled for the user-defined MS/MS scan and one or more DMS parameters necessary to enable DMS device 510 for the corresponding compound of interest of the user-defined MS/MS scan.

During the MS/MS scan step, for each user-defined MS/MS scan of the one or more user-defined MS/MS scans, processor 530 enables or disables DMS device 510 according to the DMS enable parameter of the user-defined MS/MS scan and sets one or more parameters of DMS device 510 according to the one or more DMS parameters of the user-defined MS/MS scan.

In various embodiments, the DMS enable parameter comprises an SV. An RF voltage of zero for the SV disables DMS device 510. An RF voltage greater than zero for SV the enables DMS device 510 and specifies SV setting of DMS device 510 needed to select the corresponding compound of interest of the user-defined MS/MS scan.

In various alternative embodiments, the one or more DMS parameters necessary to enable DMS device 510 for the corresponding compound of interest of the user-defined MS/MS scan comprise a separation voltage (SV) parameter and a compensation voltage (CoV) parameter.

In various alternative embodiments, the plurality of user-defined MS/MS scans can include primary and secondary scans. The plurality of user-defined MS/MS scans include one or more primary user-defined MRM scans and one or more user-defined secondary MS/MS scans. The secondary MS/MS scans can be MRM scans or full product ion MS/MS scans, for example. Each primary user-defined MRM scan of the one or more primary user-defined MRM scans includes a DMS enable parameter that disables DMS device 510 for the user-defined primary MRM scan. Each primary user-defined MRM scan also includes a triggering parameter that specifies at least one of the one or more user-defined secondary MS/MS scans to be triggered, when the product ion intensity of the user-defined primary MRM scan is measured above a predetermined product ion intensity threshold. Each secondary user-defined MS/MS scan of the one or more secondary user-defined MS/MS scans includes a DMS enable parameter that enables DMS device 510 for the user-defined secondary user-defined MS/MS scan.

In various alternative embodiments, system 500 dynamically sets or resets a DMS enable parameter based on a library search. System 500 further includes a library or database of known compounds that includes a known product ion spectrum for each known compound that is accessible to processor 530. If during the MS/MS scan step, a user-defined full product ion MS/MS scan of the plurality of user-defined MS/MS scans includes a DMS enable parameter that disables DMS device 510 for the user-defined full product ion MS/MS scan and is performed by the mass spectrometer for a compound of interest found in the precursor ion mass spectrum, processor 530 then performs a number of steps.

Processor 530 first obtains the measured product ion spectrum of the user-defined full product ion MS/MS scan. Processor 530 then searches the database for a known product ion spectrum of the compound of interest and compares the known product ion spectrum to the measured product ion spectrum. Finally, if the known product ion spectrum does not match the measured product ion within a predetermined threshold level, processor 530 sets the DMS enable parameter of the user-defined full product ion MS/MS scan to a value that enables DMS device 510 for subsequent scans of the user-defined full product ion MS/MS scan.

Method for IDA Triggered DMS Switching

Figure 6:
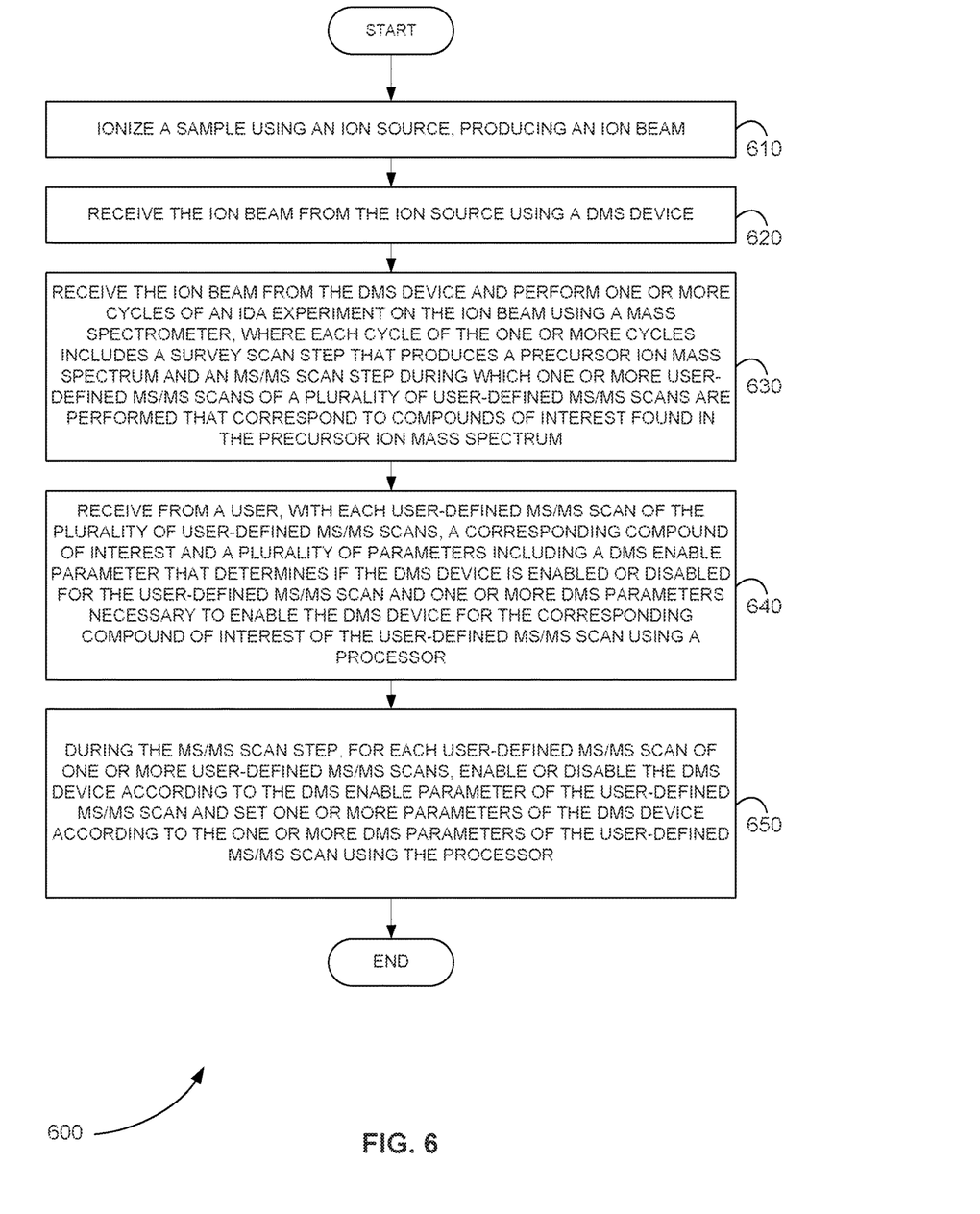
FIG. 6 is an exemplary flowchart showing a method for enabling or disabling a DMS device during an IDA experiment based on each MS/MS scan performed, in accordance with various embodiments.

FIG. 6 is an exemplary flowchart showing a method 600 for enabling or disabling a DMS device during an IDA experiment based on each MS/MS scan performed, in accordance with various embodiments.

In step 610, a sample is ionized using an ion source, producing an ion beam.

In step 620, the ion beam is received from the ion source using a DMS device.

In step 630, the ion beam is received from the DMS device and one or more cycles of an IDA experiment are performed on the ion beam using a mass spectrometer. Each cycle of the one or more cycles includes a survey scan step that produces a precursor ion mass spectrum and an MS/MS scan step. During the MS/MS scan step, one or more user-defined MS/MS scans of a plurality of user-defined MS/MS scans are performed that correspond to compounds of interest found in the precursor ion mass spectrum.

In step 640, with each user-defined MS/MS scan of the plurality of user-defined MS/MS scans, a corresponding compound of interest and a plurality of parameters are received from a user. The plurality of parameters include a DMS enable parameter that determines if the DMS device is enabled or disabled for the user-defined MS/MS scan and one or more DMS parameters necessary to enable the DMS device for the corresponding compound of interest of the user-defined MS/MS scan using a processor.

In step 650, during the MS/MS scan step, for each user-defined MS/MS scan of one or more user-defined MS/MS scans, the DMS device is enabled or disabled according to the DMS enable parameter of the user-defined MS/MS scan and the one or more parameters of the DMS device are set according to the one or more DMS parameters of the user-defined MS/MS scan.

Computer Program Product for IDA Triggered DMS Switching

In various embodiments, computer program products include a non-transitory and tangible computer-readable storage medium whose contents include a program with instructions being executed on a processor so as to perform a method for enabling or disabling a DMS device during an IDA experiment based on each MS/MS scan performed. This method is performed by a system that includes one or more distinct software modules.

Figure 7:
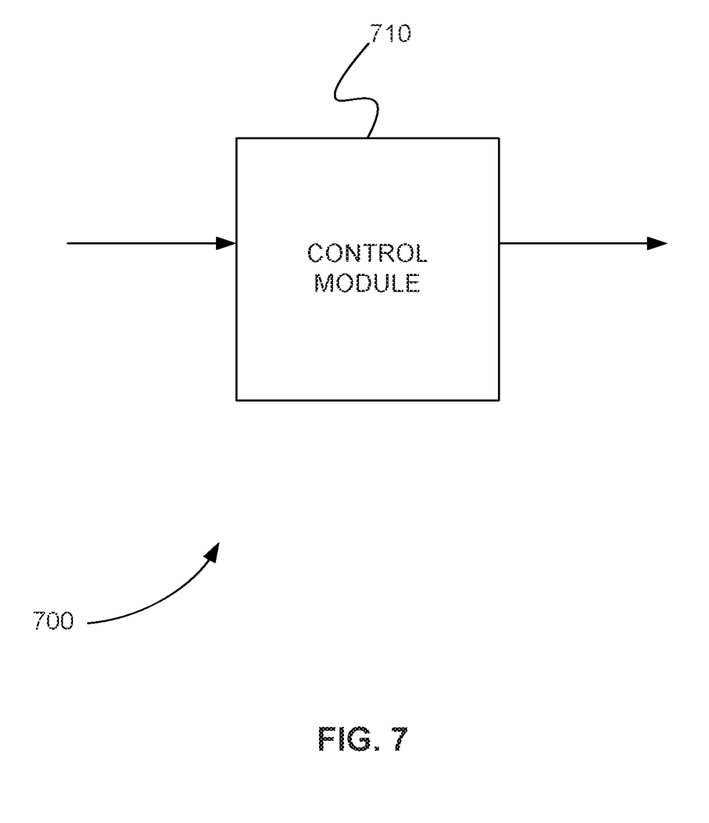
FIG. 7 is a schematic diagram of a system that includes one or more distinct software modules that perform a method for enabling or disabling a DMS device during an IDA experiment based on each MS/MS scan performed, in accordance with various embodiments.

FIG. 7 is a schematic diagram of a system 700 that includes one or more distinct software modules that perform a method for enabling or disabling a DMS device during an IDA experiment based on each MS/MS scan performed, in accordance with various embodiments. System 700 includes a control module 710.

Control module 710 instructs an ion source to ionize a sample, producing an ion beam. Control module 710 instructs a DMS device to receive the ion beam from the ion source. Control module 710 instructs a mass spectrometer to receive the ion beam from the DMS device and perform one or more cycles of an IDA experiment on the ion beam. Each cycle of the one or more cycles includes a survey scan step that produces a precursor ion mass spectrum and an MS/MS scan step. During the MS/MS scan step, one or more user-defined MS/MS scans of a plurality of user-defined MS/MS scans are performed that correspond to compounds of interest found in the precursor ion mass spectrum.

Control module 710 receives from a user, with each user-defined MS/MS scan of the plurality of user-defined MS/MS scans, a corresponding compound of interest and a plurality of parameters. The plurality of parameters include a DMS enable parameter that determines if the DMS device is enabled or disabled for the user-defined MS/MS scan and one or more DMS parameters necessary to enable the DMS device for the corresponding compound of interest of the user-defined MS/MS scan. During the MS/MS scan step, for each user-defined MS/MS scan of one or more user-defined MS/MS scans, control module 710 enables or disables the DMS device according to the DMS enable parameter of the user-defined MS/MS scan and sets one or more parameters of the DMS device according to the one or more DMS parameters of the user-defined MS/MS scan.

While the present teachings are described in conjunction with various embodiments, it is not intended that the present teachings be limited to such embodiments. On the contrary, the present teachings encompass various alternatives, modifications, and equivalents, as will be appreciated by those of skill in the art. This includes alternative methods of ion mobility or differential mobility where activation would be applied to subset of acquisition modes, based on the MRM signal monitored.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for enabling or disabling a differential mobility spectrometry (DMS) device during an information dependent acquisition (IDA) experiment based on each mass spectrometry/mass spectrometry (MS/MS) scan performed, comprising:
    an ion source that ionizes a sample producing an ion beam;
    a DMS device that receives the ion beam from the ion source;
    a mass spectrometer that receives the ion beam from the DMS device and performs one or more cycles of an IDA experiment on the ion beam, wherein each cycle of the one or more cycles includes a survey scan step that produces a precursor ion mass spectrum and an MS/MS scan step during which one or more user-defined MS/MS scans of a plurality of user-defined MS/MS scans are performed that correspond to compounds of interest found in the precursor ion mass spectrum; and
    a processor in communication with the mass spectrometer and the DMS device that
        receives from a user, with each user-defined MS/MS scan of the plurality of user-defined MS/MS scans, a corresponding compound of interest and a plurality of parameters including a DMS enable parameter that determines if the DMS device is enabled or disabled for the user-defined MS/MS scan and one or more DMS parameters necessary to enable the DMS device for the corresponding compound of interest of the user-defined MS/MS scan and
        during the MS/MS scan step, for each user-defined MS/MS scan of the one or more user-defined MS/MS scans, enables or disables the DMS device according to the DMS enable parameter of the user-defined MS/MS scan and sets one or more parameters of the DMS device according to the one or more DMS parameters of the user-defined MS/MS scan.

2. The system of claim 1, wherein the plurality of user-defined MS/MS scans comprise one or more user-defined multiple reaction monitoring (MRM) scans.

3. The system of claim 1, wherein the plurality of user-defined MS/MS scans comprise one or more user-defined full product ion MS/MS scans.

4. The system of claim 1, wherein the DMS enable parameter comprises a separation voltage (SV), wherein a radio frequency (RF) voltage of zero for the SV disables the DMS device and an RF voltage greater than zero for SV the enables the DMS device and specifies the DMS device SV setting needed to select the corresponding compound of interest of the user-defined MS/MS scan.

5. The system of claim 1, wherein the one or more DMS parameters necessary to enable the DMS device for the corresponding compound of interest of the user-defined MS/MS scan comprise a separation voltage (SV) parameter and a compensation voltage (CoV) parameter.

6. The system of claim 1,
    wherein the plurality of user-defined MS/MS scans comprise one or more primary user-defined multiple reaction monitoring (MRM) scans and one or more user-defined secondary MS/MS scans,
    wherein each primary user-defined MRM scan of the one or more primary user-defined MRM scans includes a DMS enable parameter that disables the DMS device for the user-defined primary MRM scan and a triggering parameter that specifies at least one of the one or more user-defined secondary MS/MS scans to be triggered when the product ion intensity of the user-defined primary MRM scan is measured above a predetermined product ion intensity threshold, and
    wherein each secondary user-defined MS/MS scan of the one or more secondary user-defined MS/MS scans includes a DMS enable parameter that enables the DMS device for the user-defined secondary user-defined MS/MS scan.

7. The system of claim 1, further including
    a database of known compounds that includes a known product ion spectrum for each known compound that is accessible to the processor,
    wherein, if during the MS/MS scan step, a user-defined full product ion MS/MS scan of the plurality of user-defined MS/MS scans includes a DMS enable parameter that disables the DMS device for the user-defined full product ion MS/MS scan and is performed by the mass spectrometer for a compound of interest found in the precursor ion mass spectrum, the processor obtains the measured product ion spectrum of the user-defined full product ion MS/MS scan, searches the database for a known product ion spectrum of the compound of interest, and compares the known product ion spectrum to the measured product ion spectrum and
    wherein if the known product ion spectrum does not match the measured product ion within a predetermined threshold level, the processor sets the DMS enable parameter of the user-defined full product ion MS/MS scan to a value that enables the DMS device for subsequent scans of the user-defined full product ion MS/MS scan.

8. A method for enabling or disabling a differential mobility spectrometry (DMS) device during an information dependent acquisition (IDA) experiment based on each mass spectrometry/mass spectrometry (MS/MS) scan performed, comprising:

ionizing a sample using an ion source, producing an ion beam;

receiving the ion beam from the ion source using a DMS device;

receiving the ion beam from the DMS device and performing one or more cycles of an IDA experiment on the ion beam using a mass spectrometer, wherein each cycle of the one or more cycles includes a survey scan step that produces a precursor ion mass spectrum and an MS/MS scan step during which one or more user-defined MS/MS scans of a plurality of user-defined MS/MS scans are performed that correspond to compounds of interest found in the precursor ion mass spectrum;

receiving from a user, with each user-defined MS/MS scan of the plurality of user-defined MS/MS scans, a corresponding compound of interest and a plurality of parameters including a DMS enable parameter that determines if the DMS device is enabled or disabled for the user-defined MS/MS scan and one or more DMS parameters necessary to enable the DMS device for the corresponding compound of interest of the user-defined MS/MS scan using a processor; and during the MS/MS scan step, for each user-defined MS/MS scan of one or more user-defined MS/MS scans, enabling or disabling the DMS device according to the DMS enable parameter of the user-defined MS/MS scan and setting one or more parameters of the DMS device according to the one or more DMS parameters of the user-defined MS/MS scan using the processor.

9. The method of claim 8, wherein the plurality of user-defined MS/MS scans comprise one or more user-defined multiple reaction monitoring (MRM) scans.

10. The method of claim 8, wherein the plurality of user-defined MS/MS scans comprise one or more user-defined full product ion MS/MS scans.

11. The method of claim 8, wherein the DMS enable parameter comprises a separation voltage (SV), wherein a radio frequency (RF) voltage of zero for the SV disables the DMS device and an RF voltage greater than zero for SV the enables the DMS device and specifies the DMS device SV setting needed to select the corresponding compound of interest of the user-defined MS/MS scan.

12. The method of claim 8, wherein the one or more DMS parameters necessary to enable the DMS device for the corresponding compound of interest of the user-defined MS/MS scan comprise a separation voltage (SV) parameter and a compensation voltage (CoV) parameter.

13. The method of claim 8,
wherein the plurality of user-defined MS/MS scans comprise one or more primary user-defined multiple reaction monitoring (MRM) scans and one or more user-defined secondary MS/MS scans,
wherein each primary user-defined MRM scan of the one or more primary user-defined MRM scans includes a DMS enable parameter that disables the DMS device for the user-defined primary MRM scan and a triggering parameter that specifies at least one of the one or more user-defined secondary MS/MS scans to be triggered when the product ion intensity of the user-defined primary MRM scan is measured above a predetermined product ion intensity threshold, and wherein each secondary user-defined MS/MS scan of the one or more secondary user-defined MS/MS scans includes a DMS enable parameter that enables the DMS device for the user-defined secondary user-defined MS/MS scan.

14. The method of claim 8, further comprising
if during the MS/MS scan step, a user-defined full product ion MS/MS scan of the plurality of user-defined MS/MS scans includes a DMS enable parameter that disables the DMS device for the user-defined full product ion MS/MS scan and is performed by the mass spectrometer for a compound of interest found in the precursor ion mass spectrum,
obtaining the measured product ion spectrum of the user-defined full product ion MS/MS scan using the processor,
searching a database of known compounds that includes a known product ion spectrum for each known compound for a known product ion spectrum of the compound of interest using the processor, and
comparing the known product ion spectrum to the measured product ion spectrum using the processor, and
if the known product ion spectrum does not match the measured product ion within a predetermined threshold level, setting the DMS enable parameter of the user-defined full product ion MS/MS scan to a value that enables the DMS device for subsequent scans of the user-defined full product ion MS/MS scan using the processor.

15. A computer program product, comprising a non-transitory and tangible computer-readable storage medium whose contents include a program with instructions being executed on a processor so as to perform a method for enabling or disabling a differential mobility spectrometry (DMS) device during an information dependent acquisition (IDA) experiment based on each mass spectrometry/mass spectrometry (MS/MS) scan performed, the method comprising:

providing a system, wherein the system comprises one or more distinct software modules, and wherein the distinct software modules comprise a control module;

instructing an ion source to ionize a sample using the control module, producing an ion beam;

instructing a DMS device to receive the ion beam from the ion source using the control module;

instructing a mass spectrometer to receive the ion beam from the DMS device and perform one or more cycles of an IDA experiment on the ion beam using the control module, wherein each cycle of the one or more cycles includes a survey scan step that produces a precursor ion mass spectrum and an MS/MS scan step during which one or more user-defined MS/MS scans of a plurality of user-defined MS/MS scans are performed that correspond to compounds of interest found in the precursor ion mass spectrum;

receiving from a user, with each user-defined MS/MS scan of the plurality of user-defined MS/MS scans, a corresponding compound of interest and a plurality of parameters including a DMS enable parameter that determines if the DMS device is enabled or disabled for the user-defined MS/MS scan and one or more DMS parameters necessary to enable the DMS device for the corresponding compound of interest of the user-defined MS/MS scan using the control module; and during the MS/MS scan step, for each user-defined MS/MS scan of one or more user-defined MS/MS scans, enabling or disabling the DMS device according to the DMS enable parameter of the user-defined MS/MS scan and setting one or more parameters of the DMS device according to the one or more DMS parameters of the user-defined MS/MS scan using the control module.

\* \* \* \* \*